(12) United States Patent
Knebel

(10) Patent No.: US 6,503,456 B1
(45) Date of Patent: Jan. 7, 2003

(54) MICROPLATE WITH TRANSPARENT BASE

(75) Inventor: Günther Knebel, Nürtingen (DE)

(73) Assignee: Greiner Bio-One GmbH (DE)

( * ) Notice: Subject to any disclaimer, the term of this patent is extended or adjusted under 35 U.S.C. 154(b) by 0 days.

(21) Appl. No.: 09/381,364

(22) PCT Filed: Feb. 11, 1998

(86) PCT No.: PCT/EP98/00749
§ 371 (c)(1),
(2), (4) Date: Nov. 2, 1999

(87) PCT Pub. No.: WO98/42442
PCT Pub. Date: Oct. 1, 1998

(30) Foreign Application Priority Data

Mar. 25, 1997 (DE) .......................................... 197 12 484

(51) Int. Cl.[7] .............................. B01L 3/00; B01L 11/00
(52) U.S. Cl. .......................... 422/102; 422/99; 422/101; 422/104
(58) Field of Search .................... 422/99, 101, 102, 422/104; 435/288.4, 288.3, 305.1, 305.2

(56) References Cited

U.S. PATENT DOCUMENTS

| | | | |
|---|---|---|---|
| 4,725,388 A | 2/1988 | Nelson | 264/21 |
| 4,735,778 A | 4/1988 | Maruyama | 422/102 |
| 4,948,442 A | 8/1990 | Manns | 156/73.1 |
| 5,319,436 A | 6/1994 | Manns et al. | 356/246 |
| 5,417,923 A | 5/1995 | Bojanic et al. | 422/101 |
| 5,487,872 A | 1/1996 | Hafeman | 422/102 |
| 5,508,197 A | 4/1996 | Hansen et al. | 435/285.1 |
| 5,540,891 A | 7/1996 | Portmann et al. | 422/102 |
| 5,858,309 A | * 1/1999 | Mathus et al. | 422/102 |
| 5,989,854 A | * 11/1999 | Cook | 435/35 |
| 6,051,191 A | * 4/2000 | Ireland | 422/102 |

FOREIGN PATENT DOCUMENTS

| | | |
|---|---|---|
| DE | 2733214 | 6/1978 |
| DE | 4217868 | 12/1993 |
| DE | 9409089.0 | 12/1994 |
| EP | 0131934 A2 | 1/1985 |
| EP | 0408940 A1 | 1/1991 |
| EP | 0571661 | 12/1993 |
| EP | 0723812 | 7/1996 |
| JP | 59132335 | 7/1984 |
| JP | 61126450 | 6/1986 |
| JP | 266430 | 3/1990 |
| JP | 7190924 | 7/1995 |
| JP | 8129014 | 5/1996 |
| JP | 8504955 | 5/1996 |
| JP | 8196299 | 8/1996 |
| WO | 9503538 | 2/1995 |
| WO | 9517253 | 6/1995 |

* cited by examiner

Primary Examiner—John Kim
(74) Attorney, Agent, or Firm—Ostrolenk, Faber, Gerb & Soffen, LLP

(57) ABSTRACT

The present invention relates to an improved microplate, which is constructed from at least one frame part and at least one base part, the base part having a thickness of at most 500 μm.

18 Claims, 6 Drawing Sheets

Figure 4:
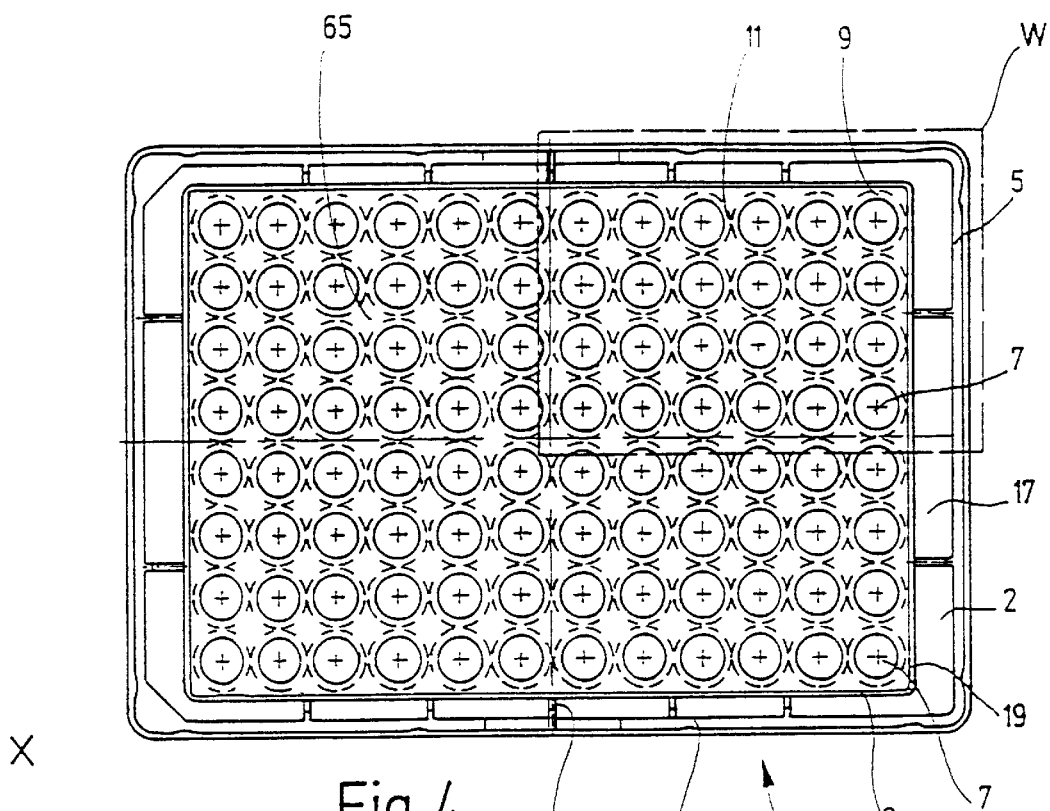

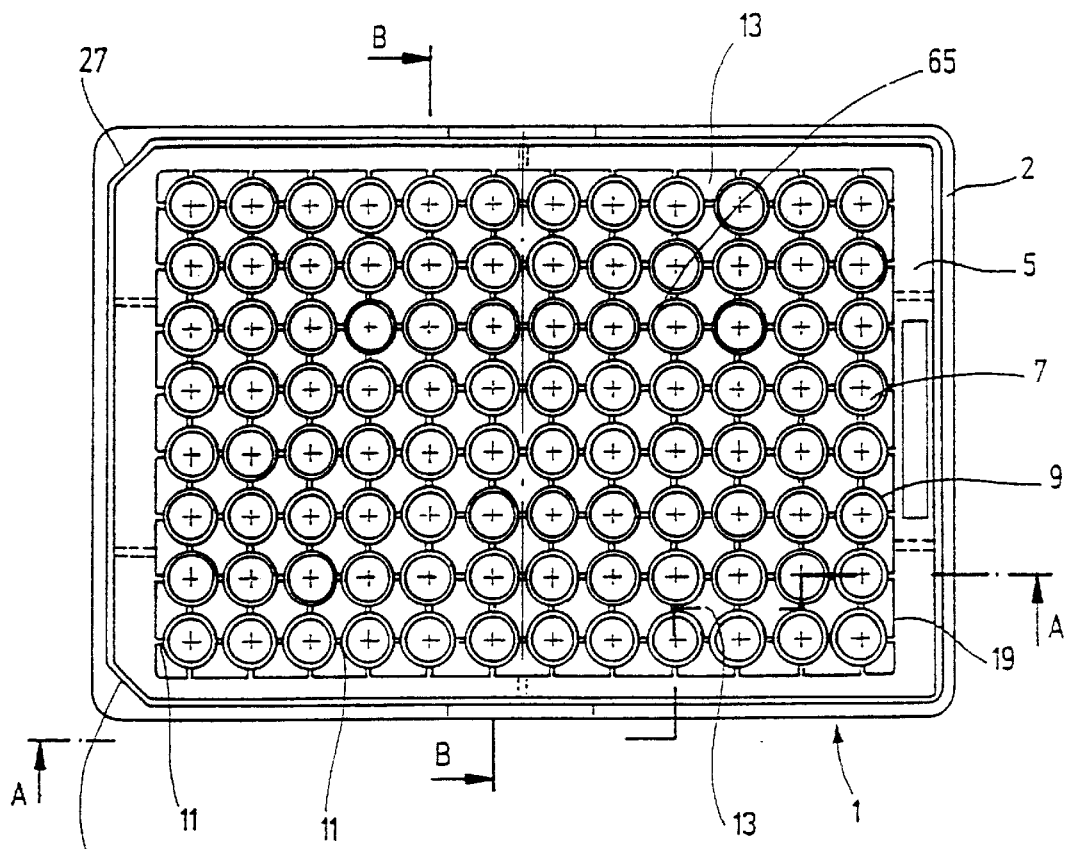
Fig. 1
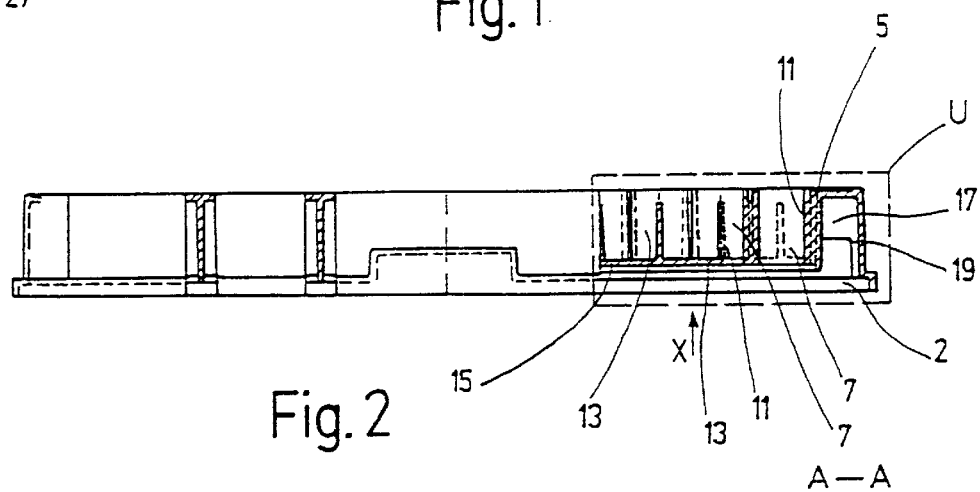
Fig. 2   A—A
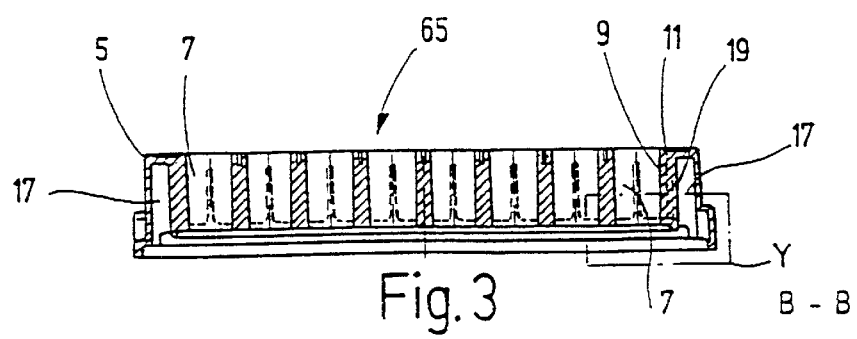
Fig. 3   B—B

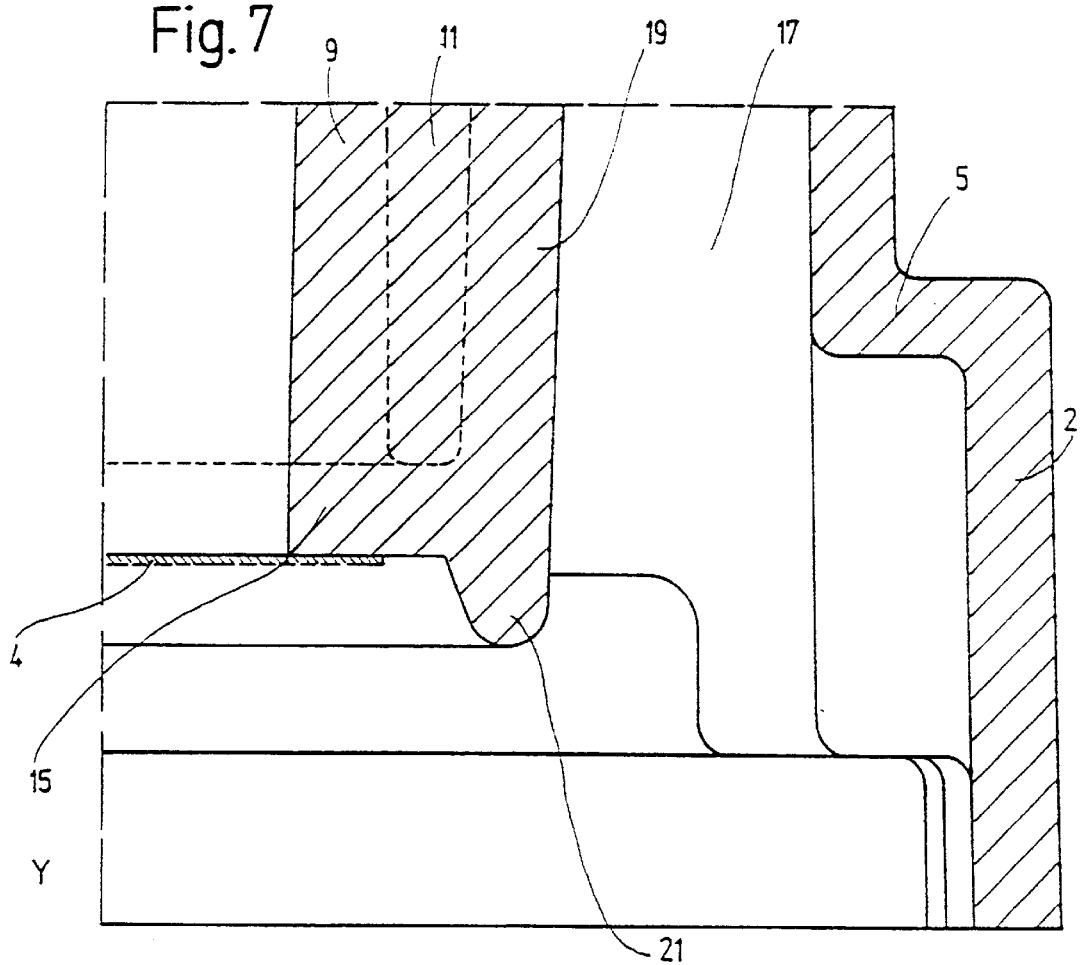
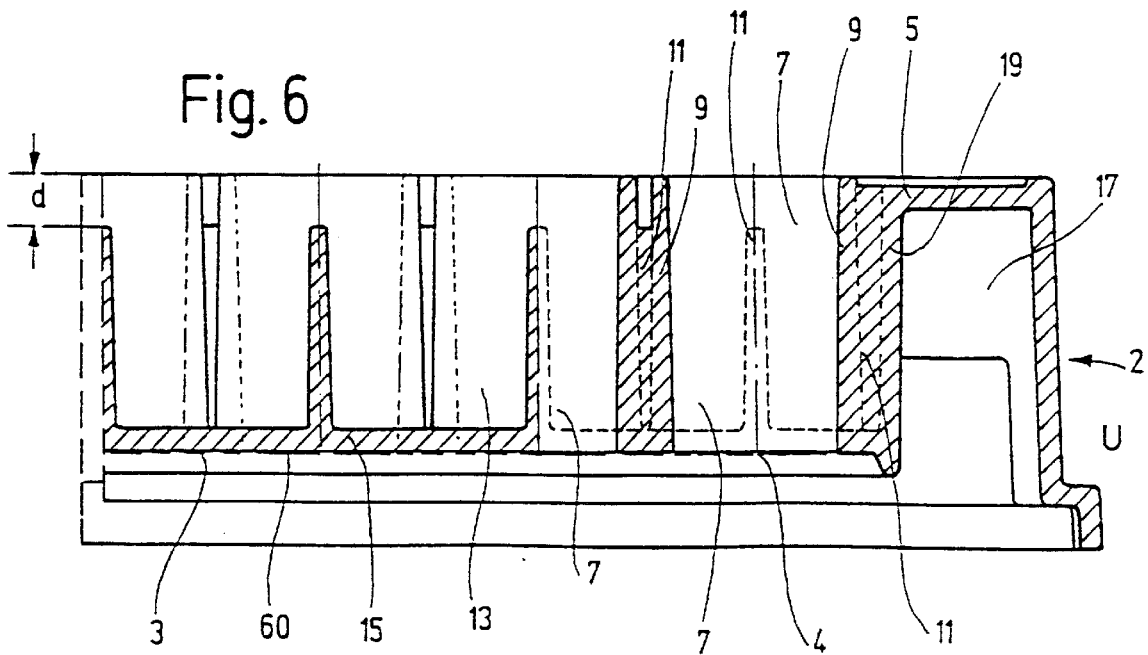

MICROPLATE WITH TRANSPARENT BASE

DESCRIPTION

The invention relates to a microplate with a particularly high packing density with a transparent base and to a process for its production.

Microplates, which are used for fluorescence, luminescence or scintillation measurements, for example in biochemical or molecular-biology questions, are known.

More recent luminescence and fluorescence techniques require the provision of dyed microplates with a transparent base. Microplates with ninety-six depressions currently constitute a standardized platform for the automatic or manual determination and evaluation of patient samples in widespread analyzers. A current method for the production of dyed microplates with a transparent base is the ultrasonic welding of a dyed plate frame to a transparent base. Both parts are preferably produced from polystyrene. However, the problem which occurs again and again is the absolute sealing of the ninety-six depressions with respect to one another. Double welded ribs are therefore often applied in order to achieve greater reliability.

EP 0 571 661 A1 discloses a microplate which can be used in measurement techniques in which light emission or translucency are determined. The microplate disclosed comprises an upper, opaque frame part forming a cell and a translucent base part, which has been welded to the upper frame part by means of ultrasound. Also known are variants of these microplates in which a protective grid produced from non-transparent material is fitted underneath the transparent base part and leaves optical windows free. It is also known to produce microplates of this type in the multi-component injection molding process, the frame and base parts being produced by means of two injection moldings and joined together.

In the case of the known microplates, it has proven to be disadvantageous that the transparent base parts, because of their thickness of about 1 mm, exhibit light conduction effects which are based on the refraction of light and on total reflection. Total reflection always occurs when light from an optically more dense medium falls onto the interface with an optically less dense medium, and the material-specific limiting angle is exceeded. This property is effectively used nowadays in light-conduction technology. Light is fed into the light conductor at one end, passes through it, because of total reflection, and can emerge again at the other end virtually unattenuated. However, the walls of the fibers must be absolutely smooth in optical dimensions for this purpose. If this is not the case, as in injection-molded parts, then the light is only partially totally reflected at each reflection, and can therefore emerge into adjacent depressions or cells. The undesired light-conduction effect also occurs, for example, in light transmission measurements, and therefore manifests itself, inter alia, in the fact that the transparent base acts as a light conductor and partially deflects light beamed into a specific cell into adjacent cells. In this connection, it has been established that as the thickness of the base increases, the light-conduction effect also increases, that is to say the measurement accuracy decreases. In addition, the known microplates, likewise because of the thickness of their transparent bases, are only conditionally suitable for radioactivity measurements, for example scintillation measurements.

The technical problem on which the present invention is based is therefore to provide microplates which overcome the above-mentioned disadvantages, in particular at the highest possible packing density, that is to say the highest possible number of depressions per microplate, which ensure a higher accuracy in the case of the optical measurements and, in addition, are also suitable for radioactive determinations.

The invention solves this problem by providing a microplate having the features of the main claim, in particular by providing a microplate having at least one frame part and at least one base part assigned to the frame part, the at least one frame part comprising a large number of cells, in particular at least 384 cells, and the at least one base part forming the bases of the cells, and the base part or, respectively, the bases of the cells having a thickness of at most 500 $\mu$m, preferably 20–500 $\mu$m, particularly preferably 40 to 100 $\mu$m.

In conjunction with the present invention, the frame part of a microplate is understood to be the part of a microplate which forms the cells or depressions, open toward the top and the bottom, in particular their side walls. The base part of a microplate is understood to be the part of a microplate which seals off the cells and, if appropriate, the cell interspaces at the bottom.

In conjunction with the present invention, a cell is understood to mean a vessel produced from any desired material, preferably plastic, which can be designed as a little bowl, depression, hole, hollow or the like and is used to hold samples to be examined.

In a particularly preferred way, the whole of the base part or only those parts of the base part which form the bases of the cells are designed as a membrane or as a film, especially a transparent film. In conjunction with the present invention, a film is understood to be a thin, preferably flexible, material layer which has no apertures, holes or the like and is accordingly impermeable to air and liquids. A film therefore has no filter function.

The invention therefore advantageously provides a microplate which, on account of the only very low thickness of the base part or, respectively, of the bases of the cells, makes a large number of advantages and applications possible. Because of the low thickness of the base part or, respectively, of the bases of the individual cells, it is for example particularly advantageously possible to carry out radioactivity determinations. If the base part is designed as a transparent film, the resultant advantage is that the undesired light-conduction effect is reduced considerably, so that the measurements can be carried out with an accuracy which is increased considerably by comparison with the prior art. If the base part is designed as a membrane, any possibly desired nutrient diffusion from below through the membrane into the (biological) cells growing on the membrane in the cell can take place particularly efficiently and largely unimpeded.

The microplates according to the invention are therefore suitable for any type of fluorescence, luminescence, colorimetric, chemiluminescence or radioactivity measurements, for example scintillation measurements. The microplates according to the invention can be used in ELISA tests, DNA and RNA hybridizations, antibody titer determinations, protein, peptide, immunological tests, PCR and cells. In particular, provision is made for the microplate according to the invention having standard dimensions (SBS standard dimensions, cf. description relating to FIG. 1) to have at least 384 cells. Of course, numbers of cells above or below this per microplate are also possible. For each frame part, it is therefore possible, for example, for there to be multiples of six, twelve, twenty-four, forty-eight or ninety-six cells, for example in a particularly advantageous embodiment 384, 768, 864, 1536 or 6144 cells.

The frame part is fitted to the base part, at most 500 µm thick, in the injection molding process, and thus closes the cells from below and at the same time provides the base for each individual cell. The microplate according to the invention may, for example, comprise such a frame part and a base part assigned to this frame part. According to the invention, however, provision may also be made to arrange one or preferably a number of frame parts removably in a base frame which is open at the center. A microplate of this type accordingly comprises a base frame and frame parts which are arranged in the base frame and are each provided with a base part.

In a further preferred embodiment, the invention provides for the frame part to be dyed white or black or else to be designed to be transparent or natural-colored. In a particularly preferred way, provision is made to produce the frame part from a material type or a material mixture which ensures an increased thermal conductivity, for example by including metal chips, such as nickel or stainless-steel chips, or carbon black.

In a particularly preferred embodiment, the invention provides for the production of the frame part from acryl-butadiene styrene (ABS), polyamide (PA), polycarbonate (PC), polystyrene (PS), polymethylmethacrylate (PMMA), polypropylene (PP) or styrene-acrylonitrile (SAN).

In a further advantageous refinement, the invention provides for the film to be designed to be transparent or dyed. According to the invention, provision may be made to use a film with an increased thermal conductivity, for example by using aluminum as the film material. In a particularly preferred embodiment of the present invention, provision is made to construct the film from a number of layers; for example, that layer of the film which faces the frame part being used for a particularly good connection to the frame part, while that layer of the film which faces away from the frame part is used for improving stability.

In a particularly preferred way, the film is produced from acryl-butadiene styrene (ABS), polyamide (PA), polycarbonate (PC), polystyrene (PS), polymethylmethacrylate (PMMA), polypropylene (PP) or styrene-acrylonitrile (SAN), and consists of these materials or their mixtures.

In a particularly preferred embodiment, the membranes provided according to the invention are produced from polyamide (PA6, PA66), polyester (PET, PETG), polycarbonate (PC), cellulose, cellulose derivative or regenerated cellulose, and consists of these materials or their mixtures.

The invention preferably provides for the base part to have a constant thickness and to be produced from the same material over its entire extent. However, the invention also provides for the base part to have the thickness envisaged by the invention of at most 500 µm only in the regions in which the base part forms the base of the respective cell, while in the regions between the cell bases and/or in the regions underneath the cell side walls, a greater thickness of the base part is provided and/or a different material composition.

In a further advantageous refinement, the invention provides for the provision, underneath the base part, of a supporting structure, which serves to stabilize the base part and can be welded or injection molded to said base part or to the frame part itself. This supporting structure advantageously leaves an optical window free in each case underneath the cell bases.

The invention further provides for at least one, preferably two, corners of the frame part or of the base frame to be bevelled or otherwise marked, so that orientation can be carried out unequivocally.

The invention also relates to a process for producing microplates from at least one frame part and at least one base part, the base part having a thickness of at most 500 µm. The invention provides for the microplates according to the invention to be produced in a single-stage process, the base part, designed as a film or membrane, being arranged in an injection molding device and a molding compound heated to 200 to 300° C., preferably 250° C., and plasticized subsequently being injection molded into the injection molding device in order to produce the frame part, and being attached to the base part.

The process according to the invention provides for a thin, prestamped film or membrane, preferably having a thickness of 60 µm, to be inserted into an injection mold and to be encapsulated by and connected to the material used for the frame part. The material can be both transparent and dyed black or white so as to be highly opaque. The fixing of the film or membrane can be carried out both using vacuum via small channel gaps, but these leave small visible imprints on the molding, and also via the electrostatic charging of the film or membrane and/or injection mold.

Using this process, it is possible for example to encapsulate polystyrene, polymethylmethacrylate, polyester or polycarbonate films or membranes in the thickness range from 20 to 500 µm. In this context, according to the invention it is preferable to provide for the film or membrane and the encapsulating molding compound to form a good connection to each other. If appropriate, according to the invention the film or membrane should be pretreated in corona or plasma processes or is to be activated using suitable adhesion promoters. The temperature resistance of the composite depends on the film or membrane and the molding compound used for the production of the frame part and, for example in the case of polystyrene, is around 50° C. It is preferable to provide for no thermal deformations of the film or membrane to occur when the heated molding compound (about 250° C.) is injected. The injection mold should be designed in such a way that the film or membrane is not displaced.

A very wide range of objectives can be implemented with this process technology by means of suitable films or membranes. These objectives include better properties of use, such as high translucency and good chemical resistance. Furthermore, the film surfaces according to the invention can be made hydrophilic or hydrophobic in plasma or corona processes, and functional amino groups can be incorporated. Microplates modified in accordance with the invention are used in immunoassays and in cell cultivation. According to the invention, it is also possible to encapsulate membranes which are to be used for cell culture techniques and filtration processes.

Any sterilization with accelerated electrons or gamma quanta which may be necessary leads to no noticeable changes in the materials.

The use of a matched mold makes it possible to produce both small series and large series cost-effectively. Different film and surface qualities can be produced in this way without any long interruption to production.

Further advantageous refinements of the invention can be taken from the subclaims.

Figure 5:
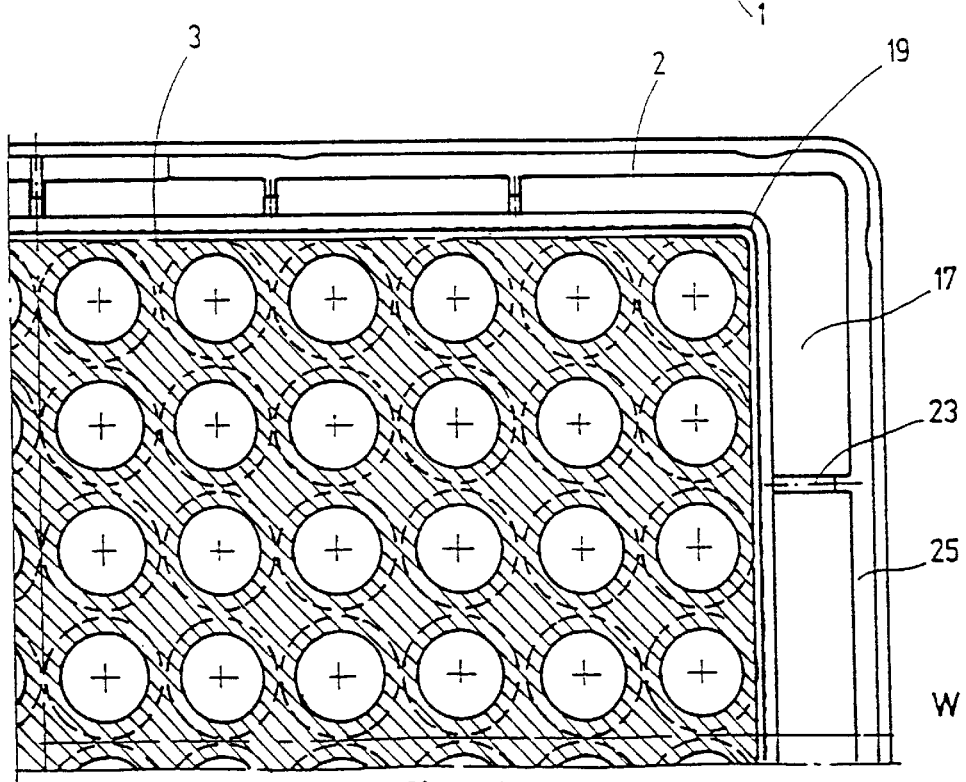
Figure 8:
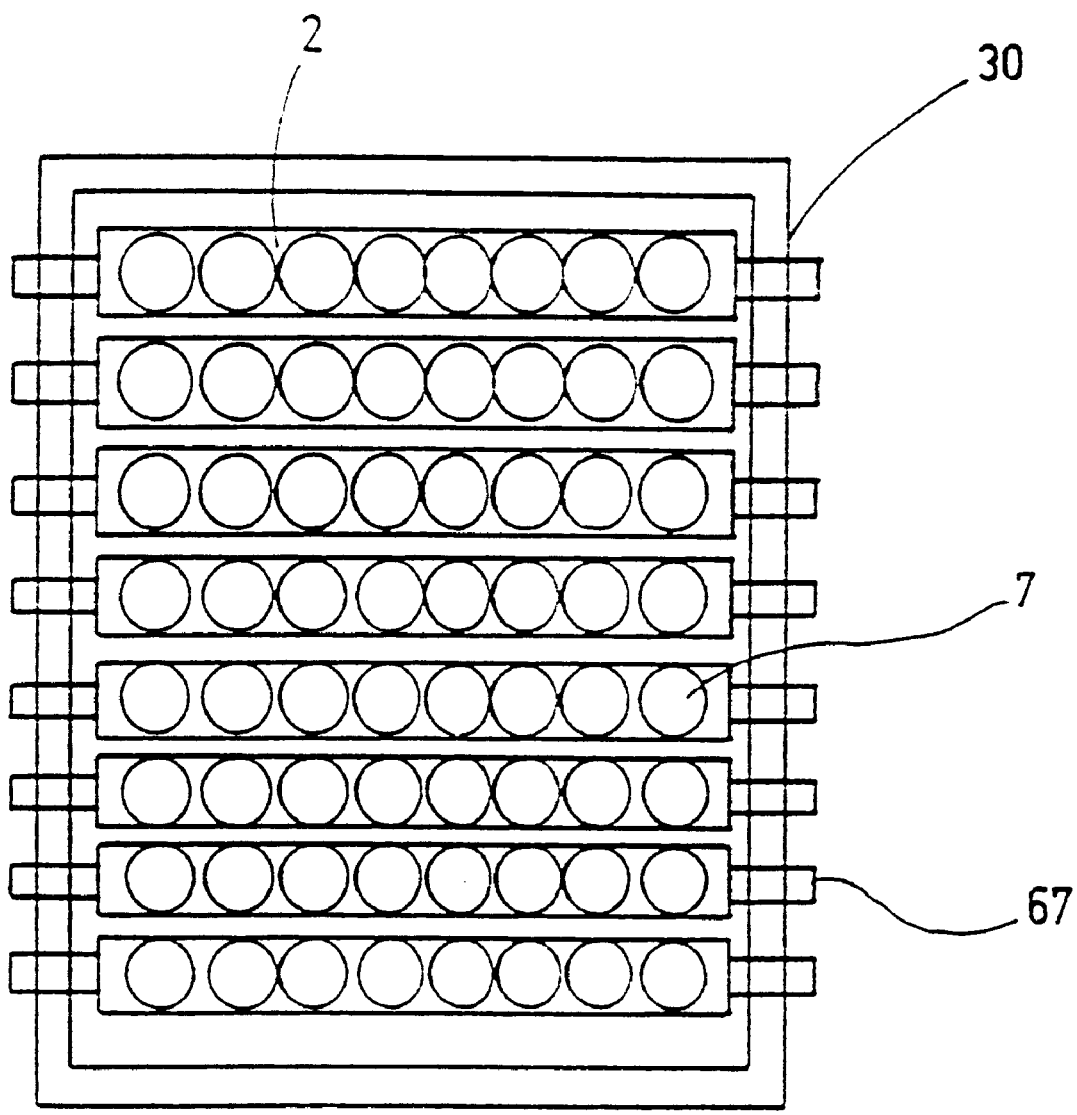
Figure 9:
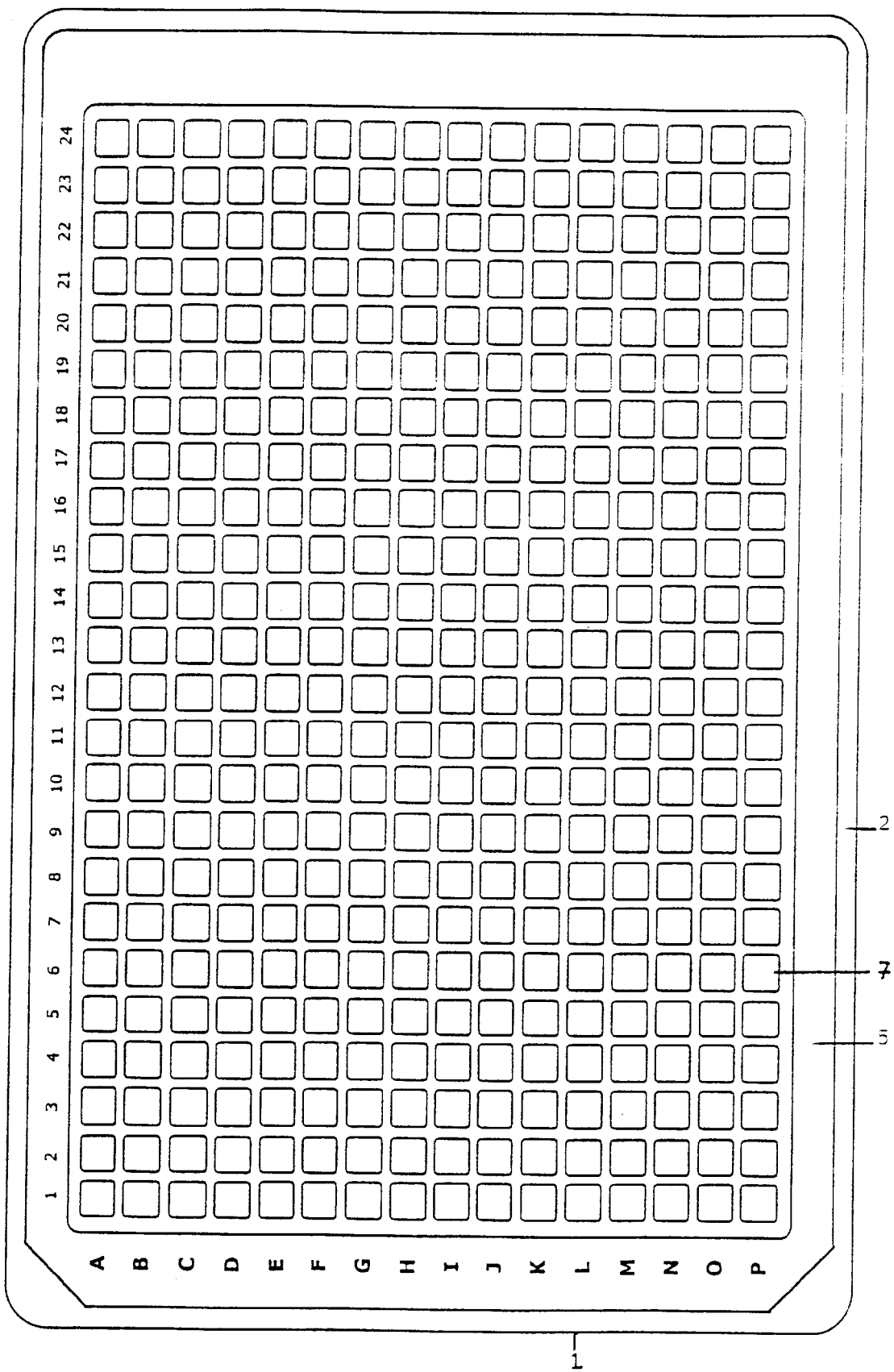
Figure 10:
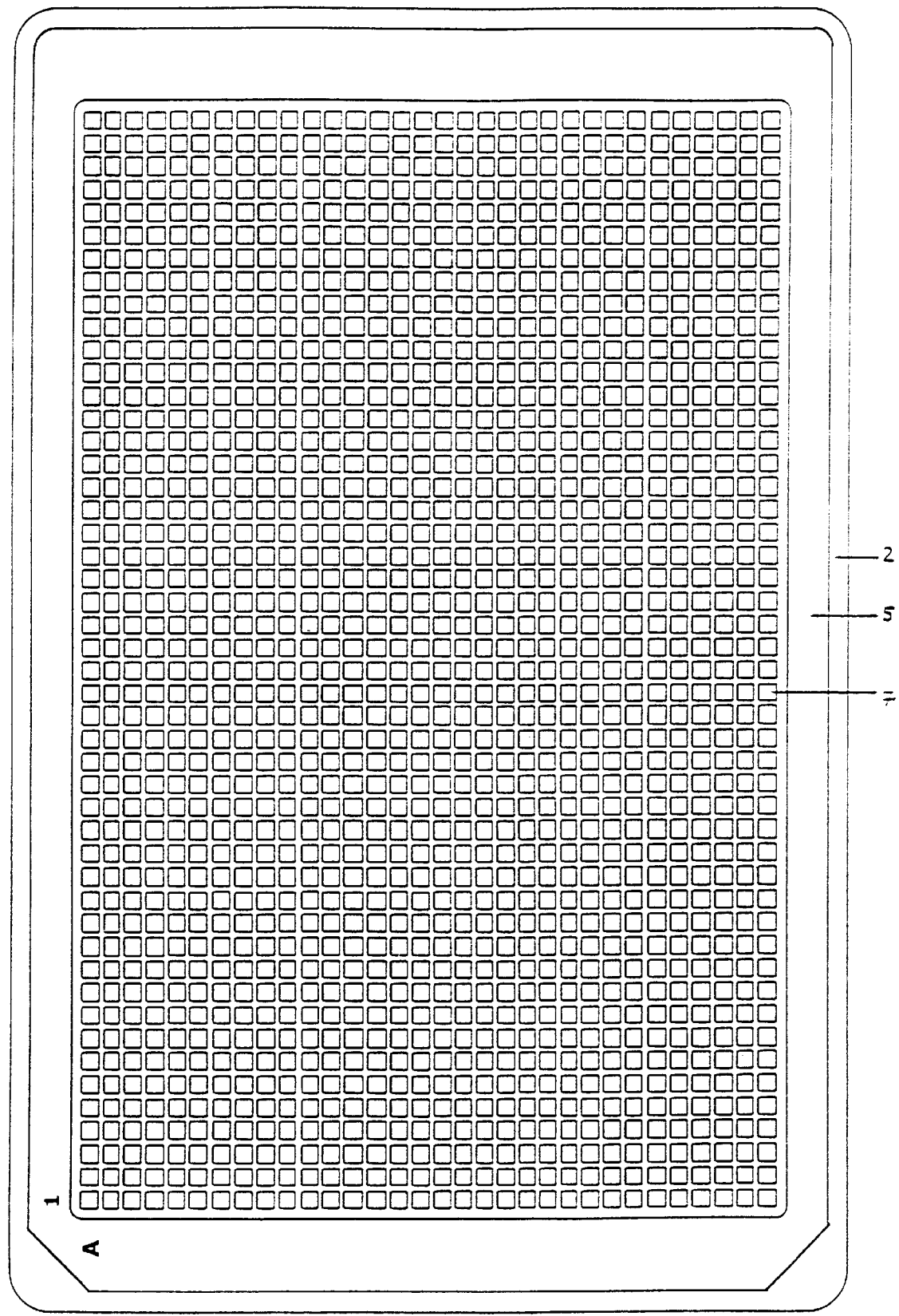

The invention will be explained in more detail using exemplary embodiments and the associated figures, in which:

FIG. 1 shows a plan view of a microplate according to the invention having 96 depressions, FIG. 2 shows an offset cross section through the microplate of FIG. 1, FIG. 3 shows a further cross section through the microplate of FIG. 1, FIG. 4 shows a view from below of the base part of the microplate according to FIG. 1, FIG. 5 shows a detail from FIG. 4, FIG. 6 shows a detail of the cross-sectional illustration of FIG. 2, FIG. 7 shows a detail from FIG. 6, FIG. 8 shows an alternative embodiment of the invention with frame parts arranged in a base frame, FIG. 9 shows a plan view of a microplate according to the invention with 384 depressions, and FIG. 10 shows a plan view of a microplate according to the invention with 1536 depressions.

FIG. 1 shows a microplate 1 having a rectangular frame part 2 which has rounded corners and is made of white, opaquely dyed polystyrene, and a base part 3 which is associated with the latter but not illustrated here. The frame part 2 is designed in one piece, complies with the standard dimensions of the SBS (Society of Biomolecular Screening) standard (MIPTEC standardization draft dated Oct. 12, 1996) and has a supporting plate 5 in which cells 7 in the form of an 8×12 matrix are formed. The cells 7, which have a circular cross section, are open toward the top, and their side walls 9 are shaped by the supporting plate 5. The cell side walls 9 are connected to the respectively adjacent cell side walls and, respectively, the frame inner wall 19 of the frame part 2 by means of webs 11. Interspaces 13 are therefore arranged between the side walls 9 of the cells 7. These interspaces 13 are open toward the top while they are closed toward the bottom by a terminating plate 15 (FIG. 2). The frame part 2 has two bevelled corners 27. The individual cells 7 can be identified by means of alphanumeric and numeric matrix labeling.

FIG. 2 represents an offset cross section through the microplate of FIG. 1. FIG. 6 shows a detail from FIG. 2. It is possible to see that the microplate 1 has, over the entire circumference in its edge region, a hollow wall 17 which is open toward the bottom and is formed by the supporting plate 5. The cells 7 having side walls 9 formed by the supporting plate 5 are in each case connected to the adjacent cells 7 or to the frame inner wall 19 via four webs 11 which are arranged at 90° to one another. The frame inner wall 19 thus likewise forms the inner side, facing the cell area, of the hollow wall 17 and encloses the entire cell area 65. It is also possible to see the interspaces 13, which are open toward the top and terminated toward the bottom by the termination plate 15 formed by the supporting plate 5. The termination plate 15 terminates only the interspaces 13 between the cells 7, but does not terminate the cells 7 themselves. It is also possible to see from FIGS. 2 and 6 that the webs 11 do not entirely reach the height of the cells 7 but end at a distance d below the top edge of the cells 7. Of course, it is also possible, depending on the geometry of the cells, to dispense with the webs, the interspaces, the termination plate and/or the frame inner wall.

FIG. 6 makes it clear that both the downwardly open cells 7 and the termination plate 15 are covered by a film 3. The film 3 has a constant thickness of 60 μm and is produced from polystyrene. The passage of light is not impeded over the entire internal diameter of the cells 7. The film 3 forms the bases 4 of the cells 7 and covers the termination plate 15 in the area 60.

FIG. 3 constitutes an offset cross section transversely to the longitudinal axis of the microplate of FIG. 1. FIG. 7 constitutes a detail from FIG. 3. Both figures likewise reveal the hollow wall 17 which is open toward the bottom, formed by the supporting plate 5 and runs around the entire circumference of the microplate 1. Also illustrated are the frame inner wall 19 that encloses the cell area 65, the webs 11 that connect the cells 7 and the side walls 9 of the cells 7. FIG. 7 shows in detail a lower corner area of the microplate 1 shown in FIG. 3. The illustration shows the hollow wall 17 formed by the supporting plate 5 of the frame part 2, together with its frame inner wall 19 and the web 11 and the side wall 9 of the cell 7. Clearly to be seen is the frame inner wall 19 which encloses the entire cell area 15 and which, with an extension 21, projects downward beyond the level of the termination plate 15. Also illustrated is the base plate 3, which is implemented as a film and covers the entire cell area 65 toward the bottom without any gaps. Both the termination plate 15 and the downwardly open cells 7 are covered by the film, so that the cells have a flat base 4.

FIG. 4 illustrates the microplate 1 from below. The illustration shows the hollow wall 17 formed by the supporting plate 5 of the frame part 2, with its frame inner wall 19. Also illustrated are connecting webs 23 between the frame inner wall 19 and the frame outer wall 25 of the frame part 2. It is possible to see the cells 7, which are covered toward the bottom by the transparent base part 3, implemented as a film, with their side wall 9 and the webs 11. It is also possible to see that the termination plate 15, which terminates the interspaces 13 toward the bottom, is covered by the base part 3.

FIG. 5 illustrates a detail of FIG. 4 and makes it clear that the base part 3 terminates the entire cell area 65 of the frame part 2 toward the bottom.

FIG. 8 illustrates a further embodiment of the invention. In a base frame 30 which is open at the center, eight units each built up from a frame part 2 and a base part 3 having eight cells in the form of a strip are arranged so that they can be removed by means of the grip surfaces 67.

FIGS. 9 and 10 illustrate microplates which likewise have standard dimensions (SBS) but contain considerably more cells. Identical or functionally similar elements are provided with identical reference symbols. FIG. 9 shows a microplate 1 which has 384 cells 7 in the form of a 16×24 matrix. The cells are square as viewed in cross section. The alphabetic and numeric labeling of the matrix is also illustrated.

FIG. 10 illustrates a microplate 1 which has 1536 cells 7, likewise with a square base surface as viewed in cross section, in the form of a 32×48 matrix.

The production of the microplate 1 was carried out as follows: a transparent polystyrene film with a thickness of 60 μm was positioned in an injection mold. The arrangement was carried out in such a way that the molding compound to be injected cannot be injected underneath the film, and relatively large dust particles were denied access into the injection chamber. In order to produce the frame part 2, polystyrene dyed white was used. This was initially heated to 260° C. in a cylinder and thus brought into a plastic state. The plasticized molding compound was then pressed out of the cylinder by means of a screw conveyor under a pressure of 1000 bar and quickly injected into the cool, closed mold, in which the film had been positioned. The molding solidified under a holding pressure loading of about 250 bar, the shrinkage of the cooling molding being compensated for by applying holding pressure to the plastic compound. The holding time until solidification was a few seconds, but in the case of large and thick-walled parts, may also be several minutes. After cooling and solidifying, the molding applied to the film is ejected.

What is claimed is:

1. A microplate having at least one frame part and at least one base part assigned to the frame part, the at least one frame part having at least 384 cells, the at least one base part being formed as a membrane or film, the base part forming the bases of the cells, the bases of the cells being formed as a membrane or film and having a thickness of at most 500 $\mu$m, the frame part having standard dimensions and containing the at least 384 cells, and a seal formed by the frame part being applied to one side of the base part in an injection molding process at a pressure of 1000 bar with a holding pressure of about 250 bar and prevented from injection underneath the base part.

2. The microplate as claimed in claim 1, wherein the membrane is comprised of polyamide, polyester, polycarbonate, cellulose, cellulose derivative or regenerated cellulose.

3. The microplate as claimed in claim 1, wherein the bases are formed as a film.

4. The microplate as claimed in claim 3, wherein the film is comprised of acryl-butadiene styrene, polyamide, polycarbonate, polystyrene, polymethylmethacrylate, polypropylene or styrene-acrylonitrile.

5. The microplate as claimed in claim 1, wherein the bases or the base part have a thickness of 20 to 500 $\mu$m.

6. The microplate as claimed in claim 1, wherein the at least one frame part is dyed white or black, or is transparent or is natural-colored.

7. The microplate as claimed in claim 1, wherein the at least one frame part has an increased thermal conductivity.

8. The microplate as claimed in claim 1, wherein the at least one frame part contains additional metal chips or carbon black.

9. The microplate as claimed in claim 1, wherein the film in transparent or dyed.

10. The microplate as claimed in claim 1, wherein the film has an increased thermal conductivity.

11. The microplate as claimed in claim 1, wherein the film is constructed from a number of layers.

12. The microplate as claimed in claim 1, further comprising a base frame which is open at its center and the at least one frame part of the microplate is arranged in the center.

13. The microplate as claimed in claim 12, wherein at least one frame part or the base frame are essentially rectangular.

14. The microplate as claimed in claim 12, wherein the cells are arranged in the frame part in a matrix form or in a row.

15. The microplate as claimed in claim 12, wherein at least one of the at least one frame part and the base frame have at least one beveled corner.

16. The microplate as claimed in claim 1, wherein the cells have a square, hexagonal or circular cross section.

17. The microplate as claimed in claim 1, further comprising a supporting structure, arranged underneath the at least one base part.

18. The microplate of claim 5, wherein the bases or the base part have a thickness of 60 $\mu$m.

* * * * *

UNITED STATES PATENT AND TRADEMARK OFFICE
Certificate t No. 6,503,456 B1                                                                 Patented: January 7, 2003 petition requesting issuance of a certificate for correction of inventorship pursuant to 35 U.S.C. 256, it
een found that the above identified patent, through error and without any deceptive intent, improperly
orth the inventorship.
:ordingly, it is hereby certified that the correct inventorship of this patent is: Günther Knebel, Nürtingen,
any; Martin Bechem, Wuppertal, Germany; Werner Stürmer, Wahlwies, Germany; and Ralph Noll,
Germany.

ied and Sealed this Twenty-seventh Day of April 2004.

*WANDA L. WALKER*
*Supervisory Patent Examiner*
Art Unit 1722/23